US008410084B2

(12) United States Patent  
Sabahi et al.

(10) Patent No.: US 8,410,084 B2  
(45) Date of Patent: Apr. 2, 2013

(54) ALKYLATED HETEROCYCLIC REACTION PRODUCTS USEFUL AS ANTIOXIDANTS

(75) Inventors: Mahmood Sabahi, Baton Rouge, LA (US); Vincent J. Gatto, Baton-Rouge, LA (US); Hassan Y. Elnagar, Baton Rouge, LA (US)

(73) Assignee: Albemarle Corporation, Baton Rouge, LA (US)

( * ) Notice: Subject to any disclaimer, the term of this patent is extended or adjusted under 35 U.S.C. 154(b) by 515 days.

(21) Appl. No.: 12/444,181

(22) PCT Filed: Oct. 17, 2007

(86) PCT No.: PCT/US2007/081603
§ 371 (c)(1),
(2), (4) Date: Apr. 3, 2009

(87) PCT Pub. No.: WO2008/048988
PCT Pub. Date: Apr. 24, 2008

(65) Prior Publication Data
US 2010/0041730 A1    Feb. 18, 2010

Related U.S. Application Data

(60) Provisional application No. 60/829,838, filed on Oct. 17, 2006.

(51) Int. Cl.
*A61K 31/33* (2006.01)
(52) U.S. Cl. ............... 514/183; 548/100; 546/1; 549/1; 540/1
(58) Field of Classification Search .............. 548/100; 540/1; 546/1; 549/1; 514/183
See application file for complete search history.

(56) References Cited

U.S. PATENT DOCUMENTS

| 2,528,769 A | 11/1950 | McCracken |
| 3,673,091 A | 6/1972 | Werzner et al. |
| 3,812,152 A | 5/1974 | Hofer et al. |
| 3,822,284 A | 7/1974 | Werzner et al. |
| 3,989,738 A | 11/1976 | Kline |
| 4,994,628 A | 2/1991 | Goddard et al. |

FOREIGN PATENT DOCUMENTS

| EP | 0269981 A | 6/1988 |
| EP | 0330613 A2 | 8/1989 |
| JP | 05331149 A | 12/1993 |
| SU | 572457 A1 | 9/1977 |

OTHER PUBLICATIONS

Decodts, Guy; "Alkytetion of Indoles With Halomethyiphenois, III, Mechanism Rearrangement of 3H-3-(P-Hydroxycenzyl) Indoles to 1H-1-(P-Hydroxybenzyl Indoles"; Bulletin De La Societe Chimique Dc France. 1 Partie—Chimie Analytique, Minerale El Physique. Societe Francaise De Chimie. Paris, FR, 1976, pp. 1839-1840, XP008078012.

Mukmeneva, N. A., et al; "Inhibiting properties of Substituted Arylamines With 3,5-di-tert-butyl-4- hydroxybenzyl Fragment,"; Aging of Polymers, Poiymer Blends and Polymer Composites, 2, 197-203 Coden: APPBCH, 2002, XP008077915.

Dinoiu,Vasile, et al; "Synthesis and ESR Spectra of Persistent Aroxyls. Part 6. 1-(3,5-Dialkyl-4-hydroxybenzyl)-pyrazole and -pyrazol-5-one Derivatives, and Their Corresponding Aroxyls"; Revue Roumaine De Chimie, 39(8),949-54, Coden: RRCHAX; ISSN: 0035-3930, 1994, XP008077988.

Herdan, Jean, et al; "4-Substituted 2,6-di-tert-butylphenols and Their Corresponding Aroxyls Possessing 4-(1-methyleneimidazolyl), 4-(1-methylenebenzimidazolyl), or 4-(1-sulfonybenzimidazolyl) Groups"; Revue Roumaine De Chimie, 28(2), 129-37; Coden: RRCHAX; ISSN: 0035-3930, 1983, XP008077976.

Bukharov, Serge V, et al; "Purposeful Synthesis of Stabilizers with Sterically Hindered Hydroxybenzyi Fragments and the Prospects for their Practical Use"; Materialy Yubileinoi Nauchno-Metoclicheskol Konferentsil "III Kirpictinikovskie Chteniya", Kazan, Russian Federation, Mar. 25-28, 2003, 97-100, Editor(s): Mukmeneva, N.A. Publisher: Kazanskii Gosederstvennyi Tekhontagicheskii Universitet. Kazan, RUS, 2003, XP008077914.

Decots, Guy, et al; "Alkylation of Indoles with Hydroxymethyl-, Aminomethyl-, and (halomethyl)phenols";Tetrahedron, 26(13), 3313-28; Coden Tetrab; ISSN:0040-4020, 1970, XP0024130528.

*Primary Examiner* — Sreeni Padmanabhan
*Assistant Examiner* — Shobha Kantamneni
(74) *Attorney, Agent, or Firm* — James A. Jubinsky

(57) ABSTRACT

This invention relates to novel macromolecular compositions having oxidation inhibition characteristics that are exhibited when added to organic material normally susceptible to oxidative degradation in the presence of air or oxygen, such a petroleum products, synthetic polymers, and elastomeric substances.

12 Claims, No Drawings

US 8,410,084 B2

ALKYLATED HETEROCYCLIC REACTION PRODUCTS USEFUL AS ANTIOXIDANTS

REFERENCE TO RELATED APPLICATION

This application is the National Stage of International Patent Appl. No. PCT/US2007/081603, filed on Oct. 17, 2007, which claims priority on U.S. Provisional Application No. 60/829,838 filed on Oct. 17, 2006, the disclosures of which are incorporated herein by reference.

FIELD OF THE INVENTION

The present invention relates to reaction products that are useful as antioxidants in organic materials normally susceptible to oxidative degradation in the presence of air or oxygen, such as petroleum products, synthetic polymers, and elastomeric substances and processes suitable for preparing such reaction products.

BACKGROUND OF THE INVENTION

It is well known that a wide variety of organic materials are susceptible to oxidative degradation in the presence of air or oxygen, especially when at elevated temperatures. Such organic materials include, for example, gasolines, diesel organic fuels, burner fuels, gas turbine and jet fuels, automatic transmission fluids, gear oils, engine lubricating oils, thermoplastic polymers, natural and synthetic rubber, and the like. Over the years, considerable efforts have been devoted to discovery and development of compounds capable of minimizing the degradation of one or more of such materials. As conditions of use and exposure of such materials to various oxygen containing environments change over the years, the desire for new effective oxidation inhibitors (a.k.a. antioxidants) continues. Also, the art benefits greatly if new and highly effective process technology is provided for producing known effective oxidation inhibitors.

U.S. Pat. No. 3,673,091 discloses forming oxidation inhibitors by the reaction between 3,5-di-tert-butyl-4-hydroxybenzyl alcohol and aryl amines, carbazole, phenazines, or acridines. Unfortunately, the resultant reaction product is a complex mixture containing large quantities of unreacted amine starting material and in which the desired products are formed in low yields.

SUMMARY OF THE INVENTION

In some embodiments, the present invention relates to macromolecular antioxidant products having properties enhancing their usefulness as oxidation inhibitors, especially for petroleum products of the types referred to above. These macromolecular reaction products comprise one or more i) heterocyclic compounds substituted with one 3,5-di-hydrocarbyl-4-hydroxylbenzyl group; ii) heterocyclic compounds substituted with two 3,5-di-hydrocarbyl-4-hydroxylbenzyl groups; iii) heterocyclic compounds substituted with three 3,5-di-hydrocarbyl-4-hydroxylbenzyl groups; iv) heterocyclic compounds substituted with four 3,5-di-hydrocarbyl-4-hydroxylbenzyl groups; v) one or more heterocyclic compounds substituted with five 3,5-di-hydrocarbyl-4-hydroxylbenzyl groups; and, vi) one or more methylene-bridged heterocyclic compounds substituted with one or more, in some embodiments in the range of from about 1 to about 12, 3,5-di-hydrocarbyl-4-hydroxylbenzyl groups.

Preferred macromolecular antioxidant products of the present invention are compounds that are liquid at room temperatures (about 23° C.) or solids that melt at less than about 100° C., preferably about 60° C., and that are capable of being dissolved in common organic solvents and especially in liquid hydrocarbon solvents. In addition, in many cases these products have higher solubility in lubricants such as, for example, a base oil consisting of 50% by volume of high viscosity index 100 Neutral and 50% by volume of high viscosity index 250 Neutral such as referred to in U.S. Pat. No. 3,673,091.

Still another aspect of this invention is the provision of new antioxidant formulations especially adapted for use in lubricating oils, and especially in lubricating oils for internal combustion engines. These and other antioxidant formulations are also described in detail hereinafter.

The above and other aspects, features, and embodiments of this invention will be still further apparent from the ensuing description and appended claims.

DETAILED DESCRIPTION OF THE INVENTION

Reaction Products of the Present Invention

As noted above, the macromolecular reaction products of the present invention are useful as antioxidants; thus, these macromolecular reaction products are sometimes referred to herein as alkylated heterocyclic compounds, antioxidant products, macromolecular antioxidant compositions, or macromolecular oxidation inhibitors for simplicity. As stated above, preferred antioxidant products of the present invention are compounds that are liquid at room temperatures (about 23° C.) or solids that melt at less than about 100° C., preferably about 60° C., and that are capable of being dissolved in common organic solvents and especially in liquid hydrocarbon solvents. In addition, in many cases these products have higher solubility in lubricants such as, for example, a base oil consisting of 50% by volume of high viscosity index 100 Neutral and 50% by volume of high viscosity index 250 Neutral such as referred to in U.S. Pat. No. 3,673,091.

The antioxidant products of the present invention typically comprise one or more heterocyclic compounds substituted with one or more 3,5-di-hydrocarbyl-4-hydroxylbenzyl group(s), and one or more heterocyclic compounds substituted with one or more 3,5-di-hydrocarbyl-4-hydroxylbenzyl group(s) and having a methylene bridge. The alkylated heterocyclic compound typically comprise one or more i) heterocyclic compounds substituted with one 3,5-di-hydrocarbyl-4-hydroxylbenzyl group; ii) heterocyclic compounds substituted with two 3,5-di-hydrocarbyl-4-hydroxylbenzyl groups; iii) heterocyclic compounds substituted with three 3,5-di-hydrocarbyl-4-hydroxylbenzyl groups; iv) heterocyclic compounds substituted with four 3,5-di-hydrocarbyl-4-hydroxylbenzyl groups; v) heterocyclic compounds substituted with five 3,5-di-hydrocarbyl-4-hydroxylbenzyl groups; and vi) one or more methylene-bridged heterocyclic compounds substituted with one or more, in some embodiments in the range of from about 1 to about 12, 3,5-di-hydrocarbyl-4-hydroxylbenzyl groups. It is preferred that the macromolecular reaction products of the present invention contain less than about 10 wt. % of heterocyclic compounds substituted with one 3,5-di-hydrocarbyl-4-hydroxylbenzyl groups, based on the total weight of the reaction product. In other embodiments the reaction products of the present invention contain 25 wt. % or less of heterocyclic compounds substituted with two 3,5-di-hydrocarbyl-4-hydroxylbenzyl groups, on the same basis. In still other embodiments the antioxidant products of the present invention contain 25 wt. % or less of heterocyclic compounds substituted with one 3,5-di-hydrocarbyl-4-hydroxylbenzyl group and heterocyclic compounds substituted with two 3,5-di-hydrocarbyl-4-hydroxylbenzyl groups, on the same basis. In some embodiments, the antioxidant products of the present invention comprise greater than 15 wt. %, in some embodiments greater than about 20 wt. % of heterocyclic compounds substituted with three 3,5-di-hydrocarbyl-4-hydroxylbenzyl groups, in other embodiments, greater than about 40 wt. %, of heterocyclic compounds substituted with four 3,5-di-hydrocarbyl-4-hydroxylbenzyl groups and heterocyclic compounds substituted with five 3,5-di-hydrocarbyl-4-hydroxylbenzyl groups, all based on the total weight of the antioxidant product. In the above embodiments, the antioxidant products of the present invention contain in the range of from about 1 to about 20 wt. %, preferably in the range of from about 1 to about 15 wt. %, and most preferably in the range of about 1 to 10 wt % of one or more methylene-bridged heterocyclic compounds substituted with one or more 3,5-di-hydrocarbyl-4-hydroxylbenzyl groups, all based on the total weight of the antioxidant product.

In some embodiments, the antioxidant products of the present invention can be described as comprising i) less than about 10 wt. %; preferably less than about 5 wt. %, more preferably less than about 1 wt. %, heterocyclic compounds substituted with one 3,5-di-hydrocarbyl-4-hydroxylbenzyl groups, all based on the total weight of the antioxidant product; ii) less than about 20 wt. %; preferably less than about 15 wt. %, more preferably less than about 10 wt. %, heterocyclic compounds substituted with two 3,5-di-hydrocarbyl-4-hydroxylbenzyl groups, all based on the total weight of the antioxidant product; iii) in the range of from about 15 wt. % to about 40 wt. %, preferably in the range of from about 15 wt. % to about 30 wt. %, more preferably in the range of from about 10 wt % to about 20 wt. % heterocyclic compounds substituted with three 3,5-di-hydrocarbyl-4-hydroxylbenzyl groups, on the same basis; iv) in the range of from about 10 wt % to about 70 wt. %, preferably in the range of from about 15 wt % to about 65 wt. %, more preferably in the range of from about 20 wt % to about 60 wt. % heterocyclic compounds substituted with four 3,5-di-hydrocarbyl-4-hydroxylbenzyl groups, on the same basis; v) in the range of from about 5 wt % to about 45 wt. %, preferably in the range of from about 8 wt % to about 40 wt. %, more preferably in the range of from about 10 wt % to about 35 wt. % heterocyclic compounds substituted with five 3,5-di-hydrocarbyl-4-hydroxylbenzyl groups, on the same basis; and vi) in the range of from about 1 wt % to about 15 wt. %, preferably in the range of from about 1 to about 10 wt. % of one or more methylene-bridged heterocyclic compounds substituted with one or more, in some embodiments in the range of from about 1 to about 12, 3,5-di-hydrocarbyl-4-hydroxylbenzyl groups, all based on the total weight of the antioxidant product.

In some embodiments, the reaction products comprise one or more compounds represented generally by Formula I:

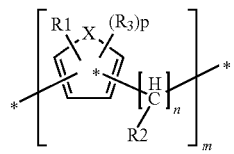

wherein X is sulfur, oxygen, or nitrogen, $R_2$ is H or hydrocarbyl, $R_3$ is 3,5-dihydrocarbyl-4-hydroxybenzyl, $R_1$ is H or hydrocarbyl, n is a whole number in the range of from about 0 to about 1, p is a whole number in the range of from about 1 to about 10, and m is 1 when n=0 and m is a whole number in the range of from about 2 to about 10 when n=1. In some embodiments, R1 is H, n=0, m=1, and p=1 and the reaction products of the present invention can be represented by Formula II:

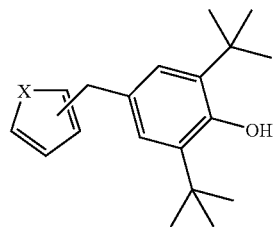

In some embodiments, X is sulfur, in some embodiments, X is oxygen, and in other embodiments, X is nitrogen.

As can be readily understood when discussing the degree of alkylation of the heterocyclic compounds in the reaction products of the present invention, the inventors hereof are referring to the "p" value. For example, if the reaction product is represented by the Formula I, a mono-alkylated heterocyclic compound would have a "p" value of 1 and be represented generally by Formula III,

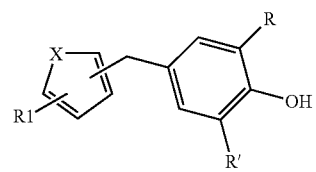

In Formula III, R and R' are independently H or hydrocarbyl, and R1 and X are as described above.

In some embodiments, the macromolecular antioxidant compositions of the present invention contain one or more, preferably two or more, compounds represented by the following general Formula IV:

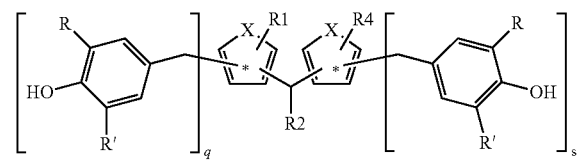

wherein R, R', R1, R2 and R4 are independently hydrogen or hydrocarbyl, q and s are whole numbers and q+s=p, and X is as described above. For example, a tetra-alkylated methylene-bridged compound represented by Formula IV may be represented by Formula V:

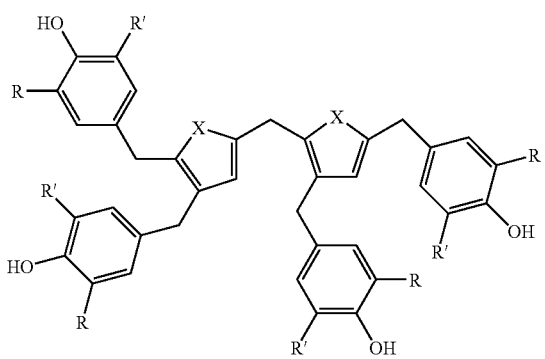

It is also obvious to the skilled in the art that the substitution pattern shown in Formulas II, III, IV, and V is for visual representation only and the alkyl and phenolic substitutions may take place on all the available active sites on the heterocyclic molecule. The skilled artisan will also recognize that in case of nitrogen containing heterocycles, it is possible to bridge through the nitrogen atom and in such cases the degree of alkylation will be two units higher than the thiophene analogs.

The antioxidant products of this invention, such as those described above, preferably have boiling points at atmospheric pressure of at least about 175° C.

Use of Reaction Products of the Present Invention

The reaction products of the present invention can be made available for use or sale as "neat" or as solutions in base oil compositions for use as an antioxidant in any organic substrate material normally susceptible to oxidative deterioration in the presence of air or oxygen. In this usage, an antioxidant quantity of a novel product of this invention can be blended with the substrate such as, for example, a lubricating oil; a liquid fuel; a thermoplastic polymer, resin or oligomer; or a natural or synthetic rubber or elastomer.

Additive compositions of this invention constitute another way of protecting such organic material against premature oxidative deterioration in the presence of air or oxygen. Thus, when adapted for use as an additive in oils, one or more reaction products of this invention can be partially diluted or dissolved in a base oil or process oil, or can be blended with other components that are commonly used in a wide variety of lubricants. Examples of base oils that may be used include Group I, II, and III mineral oils, poly-alpha-olefins, synthetic esters, gas to liquid derived oils and bio-based oils. Examples of other additives that may be used to produce new and useful lubricant additive blends with the reaction products of the invention include, but are not limited to, dispersants, detergents, anti-wear additives, extreme pressure additives, corrosion inhibitors, rust inhibitors, friction modifiers, pour point depressants, viscosity index modifiers, emulsifiers, demulsifiers, seal swell agents, solubilizing agents, antifoam agents, acid scavengers, metal deactivators, and other antioxidants or stabilizers. Combinations of one or more of these components can be used to produce additive blends with one or more of the reaction products of this invention. Also, additive compositions for use in internal combustion engine oils, railroad and marine lubricants, natural gas engine oils, gas turbine oils, steam turbine oils, aviation turbine oils, rust and oxidation oils, hydraulic fluids, compressor fluids, slideway oils, quench oils, manual and automatic transmission fluids, gear oils, greases, etc. can be formed by blending one or more of the reaction products of this invention with a diluent, solvent, or carrier fluid and/or one or more other suitable additives. The additive compositions of this invention adapted for use in oils can contain in the range of 5 wt % to 95 wt % depending upon the number and type of other components in the blend, based on the total weight of the additive composition. Finished lubricating oils of this invention will contain an antioxidant quantity of a product of this invention, which amount typically is at least about 0.1 wt %, preferably at least about 1 wt %, and more preferably at least about 3 wt % based on the total weight of the finished lubricating oil. Depending upon the type of service for which the oil of lubricating viscosity is intended, the amount of the product of this invention blended therein either as a sole additive or as an additive composition containing one or more other components will typically be no more than about 15 wt %, on the same basis.

The lubricating oil used in these embodiments of the present invention can be mineral, synthetic, or a blend of mineral and/or synthetic lubricating oils. These oils are typical industrial or crankcase lubrication oils for gas or steam turbines, transmission or hydraulic fluids, spark-ignited and compression-ignited internal combustion engines, for example natural gas engines, automobile and truck engines, marine, and railroad diesel engines. Mineral lubricating oils can be refined from aromatic, asphaltic, naphthenic, paraffinic or mixed base crudes. The lubricating oils can be distillate or residual lubricating oils, such as for example, bright stock, or blends of the oils to give a finished base stock of desired properties. Synthetic base oils used can be (i) alkyl esters of dicarboxylic acids, polyglycols and alcohols, (ii) poly-alpha-olefins, including polybutenes, (iii) alkyl benzenes, (iv) organic esters of phosphoric acids, or (v) polysilicone oils. The base oil typically has a viscosity of about 2 to about 15 cSt and preferably about 2.5 to about 11 cSt at 100° C.

Additive compositions adapted for use in forming liquid fuel compositions of this invention (e.g., gasolines, diesel fuels, jet fuels, gas turbine engine fuels, etc.) can be formed by blending therewith or providing therein an antioxidant quantity of one or more of the reaction products of this invention in the form of an additive composition of this invention comprising at least one novel compound of this invention together with one or more other additives, such as detergents, carrier fluids, demulsifiers, corrosion inhibitors, metal deactivators, lubricity agents, pour point depressants, cetane or octane improvers, antiknock agents, anti-icing agents, etc. The substrate fuels can be derived from petroleum or can be synthetic fuels, or they can be blends of both such types of materials. The amount of these new compositions in an additive blend of this invention can vary from 5 wt % to 95 wt %, based on the total weight of the additive blend, depending on the type and number of other components in the blend.

Liquid fuel compositions of this invention are typically formed by blending an antioxidant quantity of at least one of the reaction products of this invention with the fuel, either as a single additive composition (i.e., containing no other type(s) of fuel additive) or as an additive concentrate comprised of at least one of the reaction products of this invention together with at least one other type of fuel additive. The additive concentrates of this invention thus can contain in the range of about 5 to about 95 wt % of at least one of the reaction products of this invention, with the balance to 100 wt % being one or more other additives and optionally, a diluent, solvent or carrier fluid, all based on the total weight of the additive concentrate. The finished fuel compositions typically contain an antioxidant quantity in the range of about 0.0001 to about 0.1 wt %, and preferably in the range of about 0.001 to about 0.05 wt % of at least one of the reaction products of this invention, all based on the total weight of the finished fuel composition.

It will of course be understood that on blending one or more of the reaction products of this invention with a liquid substrate fuel or oil, the reaction products of this invention may no longer exist in exactly the same composition and form as they were upon addition to such substrate fuel or oil. For example, they may interact with one or more of the other components in the fuel or oil and/or they may complex with or otherwise change by virtue of becoming dissolved in the substrate fuel or oil. However, since the finished fuel or lubricant possess antioxidant properties because of the addition thereto of the one or more reaction products of this invention, the possibility of such transformations upon dilution in the substrate matters not. What matters pursuant to this invention is that whatever is formed upon such dilution is effective as an antioxidant. Consequently, expressions such as "containing in the range of", "in", etc. with reference to at least one of the reaction products of this invention are to be understood as referring to the at least one of the reaction products of this invention as it existed just prior to being blended or mixed with any liquid fuel or base oil and/or with any other component.

It will also be understood that the amount of the reaction products of this invention in a finished lubricant will vary depending upon the lubricant type, the identity of the one or more reaction products of this invention being used, and the desired level of performance required. For example, in a turbine oil, levels of the reaction product(s) of this invention often vary from about 0.05 to about 1.0 wt %, based on the total weight of the finished turbine oil. However, in an engine oil, levels typically vary from about 0.2 to about 2 wt % based on the total weight of the engine oil. In low phosphorus engine oils, levels may vary from about 0.3 to about 3 wt %, based on the total weight of the low phosphorus engine oil. In phosphorus-free engine oils levels may be as high as about 4 or 5 wt %, based on the total weight of the phosphorus-free engine oil. It will be understood that all wt. % are based on the total weight of the finished oil containing all additives, etc. When used properly the reaction products of this invention serve as antioxidant compositions. Thus, this invention also provides novel improved methods of reducing oxidation, reducing viscosity increase and polymerization, reducing acid formation and retaining lubricant basicity (TAN and TBN), reducing varnish and deposit formation, reducing friction and wear, reducing dependence on ZDDP and phosphorus for oxidation and deposit control, extending the usable life of all lubricant mentioned above, and reducing oil changes and vehicle maintenance. In each of such methods, a lubricant composition of this invention comprising an oil of lubricating viscosity with which has been blended an antioxidant quantity of at least one novel product of this invention is utilized as the lubricant. Still another method of this invention is a method of improving the oxidation stability of a lubricating oil, wherein said method comprises blending with a lubricating oil an oxidation stability improving amount of at least one reaction product of this invention. In this way the oxidation stability of the oil is significantly improved, as compared to the same oil except devoid of a reaction product of this invention.

An example of an engine oil composition of this invention is formed by blending together components that comprise:

Detergent: 0.5 to 5.0 wt % as pure component or concentrate. Concentrates typically contain 25 to 90 wt % diluent oil;

Dispersant: 1.0 to 10.0 wt % as pure component or concentrate. Concentrates typically contain 25 to 90 wt % diluent oil;

Zinc dialkyldithiophosphate (ZDDP): 0.1 to 1.5 wt % as pure component (with the lower amounts being preferred);

Viscosity Modifier as an optional component: 1.0 to 15.0 wt % as pure component or concentrate. Concentrates typically contain 5 to 50 wt % diluent oil;

Additional antioxidant(s) as one or more additional optional components: 0.01 to 1.0 wt % as pure component or concentrate. Concentrates typically contain 25 to 90 wt % diluent oil;

Additional additives as one or more optional components used in amounts sufficient to provide the intended function of the additive(s): one or more friction modifiers, supplemental anti-wear additives, anti-foam agents, seal swell agents, emulsifiers, demulsifiers, extreme pressure additives, corrosion inhibitors, acid scavengers, metal deactivators, and/or rust inhibitors;

At least one product of this invention: 0.1-2.5 wt %; with the balance to 100 wt % composed of one or more base oils. It will be understood that all wt. % are based on the total weight of the finished oil containing all additives, etc.

Also provided by this invention are novel compositions comprised of at least one reaction product of this invention combined with:

1) at least one conventional hindered phenolic antioxidant
2) at least one conventional alkylated diphenylamine antioxidant
3) at least one organomolybdenum compound
4) at least one alkylated diphenylamine and at least one organomolybdenum compound
5) at least one phosphorus-free anti-wear or extreme pressure additive
6) at least one molybdenum-containing or boron-containing dispersant
7) at least one organoboron compound
8) at least one organoboron compound and at least one conventional alkylated diphenylamine
9) at least one sulfurized antioxidant, EP (extreme pressure) additive or anti-wear additive
10) at least one conventional alkylated diphenylamine along with at least one (i) sulfurized antioxidant, (ii) EP additive, (iii) anti-wear additive, and (iv) organoboron compound.
11) at least one base oil or process oil.

It will be understood, that it is within the scope of the present invention, that the compositions described in this paragraph can contain any one of 1)-11) or combinations of any two or more of 1)-11).

Processes for Forming the Products of the Invention

The macromolecular reaction products of the present invention can be formed by, for example, using process technology comprising bringing together to form a reaction mixture, components comprising:

(A) a sterically hindered 4-alkoxymethyl-2,6-dihydrocarbylphenol, preferably a sterically hindered 4-alkoxymethyl-2,6-dialkylphenol and more preferably, a 4-alkoxymethyl-2,6-di-tert-butylphenol in which the alkoxymethyl group is ethoxymethyl or methoxymethyl, and still more preferably, 4-methoxymethyl-2,6-di-tert-butylphenol; or a sterically hindered 4-hydroxymethyl-2,6-dihydrocarbylphenol, preferably a sterically hindered 4-hydroxymethyl-2,6-dialkylphenol, and more preferably a 4-hydroxymethyl-2,6-di-tert-butylphenol and;

(B) at least one heterocyclic compound which is a monocyclic or polycyclic compound wherein:
  a) the monocyclic group of the monocyclic compound is fully conjugated and has as the sole heteroatom(s) in the fully conjugated ring thereof (i) one nitrogen atom, one sulfur atom, or one oxygen atom, (ii) one sulfur and one nitrogen atom, one sulfur and one oxygen atom, or one nitrogen and one oxygen atom, or (iii) two nitrogen atoms, two sulfur atoms, or two oxygen atoms, and
  b) at least one of the cyclic groups of the polycyclic compound is fully conjugated and has as the sole heteroatom(s) in the fully conjugated ring thereof (i) one nitrogen atom, one sulfur atom, or one oxygen atom, (ii) one sulfur and one nitrogen atom, one sulfur and one oxygen atom, or one nitrogen and one oxygen atom, or (iii) two nitrogen atoms, or two sulfur atoms, or two oxygen atoms;

(C) an alkylation catalyst, and (D) optionally, an organic solvent, such that said at least one heterocyclic compound is alkylated to form a reaction product mixture between at least one component of (A) and at least one component of (B), with co-formation of or at least one alcohol, ROH, where RO corresponds to the alkoxy group or water. Various relative proportions of (A) and (B) can be used, whereby there is a molar excess of (A) relative to (B). In preferred embodiments, (A) and (B) are used in a molar ratio of (A) to (B) in the range of about 1:1 to about 10:1, more preferably 1:1 to about 7:1.

Component (A)

The sterically hindered 4-alkoxymethyl-2,6-dihydrocarbylphenol or 4-hydroxymethyl-2,6-dihydrocarbylphenol, used as a reactant to produce the antioxidant products of this invention can be any of a relatively large group of compounds. The hydrocarbyl groups in the ortho positions relative to the carbon atom carrying the hydroxyl group can be any univalent hydrocarbon group with the proviso that the resultant substitution in the 2- and 6-positions provides steric hindrance to the hydroxyl group. Typically, a total of at least 4 or 5 carbon atoms in the ortho positions is required to achieve steric hindrance. Among suitable hydrocarbyl groups that can be in the ortho positions are alkyl, cycloalkyl, alkenyl, cycloalkenyl, cycloalkylalkyl, aryl, and aralkyl in which the cyclic moieties, whether saturated or unsaturated, can in turn be alkyl substituted. The alkyl and alkenyl groups can be linear or branched. The individual hydrocarbyl groups in the ortho positions can each contain in the range of 1 to about 12 carbon atoms with the total number of carbon atoms in the ortho positions being in the range of about 4 to about 18 carbon atoms and preferably in the range of 8 to about 16 carbon atoms. 4-Alkoxymethylphenols in which at least one of the ortho positions is substituted by a tertiary alkyl group are preferred. The alkoxy group can be linear or branched and can contain up to about 18 carbon atoms and preferably up to about 6 carbon atoms. Preferred are the 4-alkoxymethyl hindered phenols in which the alkoxy group is ethoxy, and more preferably where the alkoxy group is methoxy. Branching of alkyl or alkenyl groups can occur anywhere in the alkyl or alkenyl group, including on the alpha-carbon atom of a secondary alkyl group such as isopropyl or sec-butyl, or on more remote positions such as on the beta-position in 2-ethylhexyl. Also, there can be any number of branches in the alkyl or alkenyl group, such as, for example, the four branches in a 1,1,3,3-tetramethylbutyl group.

Non-limiting examples of suitable sterically hindered 4-alkoxymethyl-2,6-dihydrocarbylphenols include, 4-ethoxymethyl-2,6-diisopropylphenol, 4-methoxymethyl-2-tert-butyl-6-methylphenol, 4-butoxymethyl-2,6-di-tert-butylphenol, 4-hexadecyloxymethyl-2-tert-butyl-6-methylphenol, 4-decyloxymethyl-2-tert-butyl-6-isopropylphenol, 4-hexyloxymethyl-2-cyclohexyl-6-ethylphenol, 4-methoxymethyl-2-tert-butyl-6-phenylphenol, 4-propoxymethyl-2-benzyl-6-isopropylphenol, 4-ethoxymethyl-2,6-di-tert-butylphenol, 4-methoxymethyl-di-tert-butylphenol, 4-(2-ethylhexyloxymethyl)-2,6-di-tert-butylphenol, and analogous hindered phenolic compounds. A preferred sub-group of sterically hindered 4-alkoxymethyl-2,6-dialkylphenols are those in which one of the ortho alkyl groups is tert-butyl and the other is methyl or, more preferably, tert-butyl and in which the alkoxymethyl group has a total of 9 carbon atoms. Particularly preferred is 4-methoxymethyl-2-tert-butyl-6-methylphenol. In one exemplary embodiment, (A) is 4-methoxymethyl-2,6-di-tert-butylphenol.

Non-limiting examples of suitable sterically hindered 4-hydroxymethyl-2,6-dihydrocarbylphenols include, 4-hydroxymethyl-2,6-diisopropylphenol, 4-hydroxymethyl-2-tert-butyl-6-methylphenol, 4-hydroxymethyl-2,6-di-tert-butylphenol, 4-hydroxymethyl-2-tert-butyl-6-methylphenol, 4-hydroxymethyl-2-tert-butyl-6-isopropylphenol, 4-hydroxymethyl-2-cyclohexyl-6-ethylphenol, 4-hydroxymethyl-2-tert-butyl-6-phenylphenol, 4-hydroxymethyl-2-benzyl-6-isopropylphenol, 4-hydroxymethyl-2,6-di-tert-butylphenol, and analogous hindered phenolic compounds. A preferred sub-group of sterically hindered 4-hydroxymethyl-2,6-dialkylphenols are those in which one of the ortho alkyl groups is tert-butyl and the other is methyl or, more preferably, tert-butyl. Particularly preferred is 4-hydroxymethyl-2-tert-butyl-6-methylphenol. In one exemplary embodiment, (A) is 4-hydroxymethyl-2,6-di-tert-butylphenol.

Component (B)

In the practice of the present invention, (B) can be any of a number of compounds such as those described above. However, (B) is typically selected from heterocyclic compounds which are monocyclic or polycyclic compounds wherein the monocyclic group or at least one of the cyclic groups of the polycyclic compound is fully conjugated and has as the sole heteroatom(s), (i) one nitrogen atom, or one sulfur atom, or one oxygen atom, (ii) one sulfur and one nitrogen atom, one sulfur and one oxygen atom, one nitrogen and one oxygen atom, or (iii) two nitrogen atoms, or two sulfur atoms, or two oxygen atoms in the fully conjugated ring. Non-limiting examples of such compounds include pyrrole, imidazole, pyrazole, pyridine, pyrimidine, pyrazine, phenazine, thiophene, 2-benzothiophene, dibenzothiophene, dithiine, benzodithiine, indole, quinoline, acridine, carbazole, oxazole, isoxazole, thiazole, and isothiazole, furan, 2-benzofuran, 1,4-dioxin, benzodioxin, dibenzodioxin, and dibenzofuran. The rings of such compounds can be substituted by one or more electron releasing groups such as hydroxy, mercapto, alkoxy, amino, monoalkylamino, dialkylamino, and/or hydrocarbyl groups provided that at least one replaceable activated hydrogen atom remains on the ring. Non-limiting examples of such substituted compounds include 2-methylpyrrole, 2-ethylpyrrole, 2-methylpyridine, 2,4-dimethylpyridine, 2,3-dimethylpyrazine, 2-ethylpyridine, 2-methylimidazole, 2-methylfuran, 2-ethylfuran, 2,3-dimethylfuran and similar alkylated (e.g., $C_{1-12}$) heterocyclic compounds of the types referred to above.

In some processes, (B) can be selected from:

(B1) at least one heterocyclic compound which is a monocyclic, dicyclic, tricyclic or tetracyclic compound wherein the cyclic group of the monocyclic compound or at least one of the cyclic groups of the dicyclic, tricyclic or tetracyclic compound is fully conjugated and has as the sole heteroatom(s) in the fully conjugated ring thereof (i) one nitrogen atom, one sulfur atom, or one oxygen atom, (ii) one sulfur and one nitrogen atom, one sulfur and one oxygen atom, or one nitrogen and one oxygen atom, or (iii) two nitrogen atoms, two sulfur atoms, or two oxygen atoms, wherein each of (B1) (a) has at least one replaceable hydrogen atom on a ring thereof, (b) is substituted by one or more branched chain alkyl groups each having in the range of 3 to about 24 carbon atoms and preferably, in the range of 4 to about 12 carbon atoms, and (c) optionally, has one or more additional alkyl side chains each having in the range of 1 to about 3 carbon atoms.

In some embodiments (B) can be selected from:

(B2) at least one heterocyclic compound which is a monocyclic, dicyclic, tricyclic or tetracyclic compound wherein the cyclic group of the monocyclic compound or at least one of the cyclic groups of the dicyclic, tricyclic or tetracyclic compound is fully conjugated and has as the sole heteroatom(s) in the fully conjugated ring thereof (i) one nitrogen atom, one sulfur atom, or one oxygen atom, (ii) one sulfur and one nitrogen atom, one sulfur and one oxygen atom, or one nitrogen and one oxygen atom, or (iii) two nitrogen atoms, two sulfur atoms, or two oxygen atoms;

wherein (B2) has (a) at least one replaceable hydrogen atom on a ring thereof, and (b) optionally, one or more alkyl side chains each having in the range of 1 to 2 carbon atoms.

Component (C)

In the processes described herein, an alkylation catalyst is used to promote the reaction between (A) and (B), thus the reaction between (A) and (B) is sometimes referred to as an alkylation reaction herein. The alkylation reaction catalyst used herein can be selected from any alkylation catalyst known to promote the reaction of (A) and (B). In some embodiments, (C) is preferably an acidic catalyst such as sulfuric acid, an aryl sulfonic acid, an alkyl sulfonic acid, or an aryl alkyl sulfonic acid. Non-limiting examples of other suitable alkylation catalysts include, for example, hydrochloric acid, hydrobromic acid, aluminum chloride, diethyl aluminum chloride, triethylaluminum/hydrogen chloride, ferric chloride, zinc chloride, antimony trichloride, stannic chloride, boron trifluoride, acidic zeolites, acidic clays, and polymeric sulfonic acids such as those sold under the name Amberlyst®.

Component (D)

The processes of the present invention are carried out in a liquid reaction medium that can result from one of the reactants being a liquid under the conditions of the alkylation reaction, or which can result from use of an inert organic solvent. Non-limiting examples of organic solvents which can be used include, for example, acetic acid, propionic acid, one or more hexane isomers, one or more heptane isomers, one or more octane isomers, one or more decanes, mixtures of one or more of the alkane solvents such as the foregoing, cyclohexane, methylcyclohexane, methylene dichloride, methylene dibromide, bromochloromethane, 1,2-dichloroethane, 1,2-dibromoethane, chloroform, chlorobenzene, mixtures of one or more chlorinated and/or brominated solvents such as the foregoing, and one or a mixture of alkanols such as methyl alcohol, ethyl alcohol, isopropyl alcohol, n-propyl alcohol, n-butyl alcohol, sec-butyl alcohol, isobutyl alcohol, 2-ethylhexyl alcohol, octyl alcohol, and other liquid or low melting homologous alkanols, and one or more ethers like dialkyl ethers, tetrahydrofuran, dioxane or mixtures thereof. In some embodiments, the solvent is a hydrocarbon solvent. In preferred embodiments, (D) is used in the practice of the present invention.

Process Conditions

The processes described herein are conducted at one or more temperatures in the range of from about 20° C. to about 160° C. or higher. In some embodiments, the processes of the present invention are conducted at one or more temperatures above 40° C., preferably in the range of from 70° C. to about 160° C., or higher. The inventors hereof have discovered that reaction temperatures within these ranges are more suitable for producing the reaction products of the present invention. Further, the inventors hereof have discovered that at higher temperatures, i.e. greater than 40° C., the processes of the present invention proceed more rapidly and thus completion can be reached in shorter periods of time than previously contemplated. For example, when 2,6-di-tert-butyl-4-methoxymethylphenol is used as (A), the reaction tends to initiate relatively rapidly at room temperature, (about 23° C.) until about one equivalent of the 2,6-di-tert-butyl-4-methoxymethylphenol has been consumed. Thereafter, the reaction tends to proceed more slowly and consequently additional heat energy needs to be applied and/or additional catalyst employed. However, at higher temperatures, i.e. greater than 40° C., this reaction proceeds more rapidly and thus completion can be reached in shorter periods of time.

With lower boiling reactants and/or solvents the reaction may be conducted under pressure, or the reaction may be conducted in the presence of a cooling condenser. In most cases, the reaction results in alkylation on an activated, electron rich ring. In some cases, alkylation may occur on a nitrogen atom.

In the practice of the present invention, the inventors hereof have discovered that by varying the relative molar ratio of (A) to (B), one can produce various macromolecular reaction products, as described below, that find use as antioxidants. In some embodiments, (A) and (B) are used in a molar ratio of (B) to (A) in the range of about 1:1 to about 1:10, preferably in the range of from about 1:1 to about 1:7, in some embodiments, the molar ratio of (B) to (A) in the range of about 1:3 to about 1:10, preferably in the range of from about 1:3 to about 1:7. In preferred embodiments, the molar ratio of (B) to (A) can be any of about 1:1, about 1:2, about 1:2.5, about 1:3, about 1:3.5, about 1:4, about 1:4.5, about 1:5, about 1:5.5, about 1:6, about 1:6.5, or about 1:7.

The above description is directed to several embodiments of the present invention. Those skilled in the art will recognize that other means, which are equally effective, could be devised for carrying out the spirit of this invention. It should also be noted that preferred embodiments of the present invention contemplate that all ranges discussed herein include ranges from any lower amount to any higher amount.

The following examples will illustrate the present invention, but are not meant to be limiting in any manner.

EXAMPLES

The antioxidant effectiveness of the products in the following examples was analyzed by use of a standardized oxidation test procedure (ASTM D 6186) in which a lubricating oil containing a specified amount of an additive is subjected to oxidation in a heated pressure-resistant vessel at a temperature of 160° C. charged with oxygen under an initial elevated pressure of 500 psig. The longer the induction time (OIT) before a pressure drop occurs, the more stable the composition.

Example 1

Thiophene and 2,6-di-tert-butyl-4-methoxymethylphenol (1:1 Ratio)

A three-necked round-bottomed flask was equipped with an addition funnel, magnetic stirrer, temperature probe, and a condenser. Thiophene (0.1 mol, 8.4 g) was dissolved in dichloromenthane (20 mL) and sulfuric acid (3 mL of 80%) was added at room temperature. A solution of 2,6-di-tert-butyl-4-methoxymethylphenol (0.1 mol, 25 g) in dichloromethane (50 mL) was added at room temperature and in small increments. An exothermic reaction ensued during the addition of the first equivalent of 2,6-di-tert-butyl-4-methoxymethylphenol, but it subsided when the addition continued. The reaction mixture was stirred at room temperature for 3 hrs. NMR Analysis showed complete conversion of the starting materials. The acid phase was separated and the organic phase was washed with water (20 mL), dilute sodium hydroxide to pH 7-8, water (20 mL), and dried over magnesium sulfate. Evaporation of solvent under reduced pressure afforded a viscose oil which solidified on standing at room temperature, mp 54° C. HPLC Analysis showed mono-substituted isomer (13%), di-substituted isomer (18%), tri-substituted isomer (19%), tetra-substituted isomer (32%), and penta-substituted isomer (11%). In addition 6% of methylene-bridged products and other oligomeric materials were identified in the product. Oxidation Inhibition Time measured by PDSC @ 160° C. was 72 minutes at 0.25 wt %%, 115 minutes at 0.50% wt %, and 174 minutes at 0.75 wt % loading.

Example 2

Thiophene and 2,6-di-tert-butyl-4-methoxymethylphenol (1:2 ratio)

A three-necked round-bottomed flask was equipped with an addition funnel, magnetic stirrer, temperature probe, and a condenser. Thiophene (0.1 mol, 8.4 g) was dissolved in dichloromenthane (20 mL) and sulfuric acid (3 mL of 80%) was added at room temperature. A solution of 2,6-di-tert-butyl-4-methoxymethylphenol (0.2 mol, 50 g) in dichloromethane (60 mL) was added at room temperature and in small increments. An exothermic reaction ensued during the addition of the first equivalent of 2,6-di-tert-butyl-4-methoxymethylphenol, but it subsided when the addition continued. The reaction mixture was stirred at room temperature for 3 hrs. NMR Analysis showed complete conversion of the starting materials. The acid phase was separated and the organic phase was washed with water (20 mL), dilute sodium hydroxide to pH 7-8, water (20 mL), and dried over magnesium sulfate. Evaporation of solvent under reduced pressure afforded a viscose oil which solidified on standing at room temperature. The solid did not have a clear melting point but became fluid at 70° C. HPLC Analysis showed mono-substituted isomer (5%), di-substituted isomer (8%), tri-substituted isomer (13%), tetra-substituted isomer (40%), penta-substituted isomer (20%). In addition 12% of methylene-bridged products and other oligomeric materials were identified in the product. Oxidation Inhibition Time measured by PDSC @ 160° C. was 68 minutes at 0.25 wt %%, 114 minutes at 0.50% wt %, and 169 minutes at 0.75 wt % loading.

Example 3

Thiophene and 2,6-di-tert-butyl-4-methoxymethylphenol (1:2.4 ratio)

The same procedure as example 1 was used, except a thiophene/2,6-di-tert-butyl-4-methoxymethylphenol mole ratio of 1:2.4 was used. A solid product, mp 71° C., was isolated. HPLC Analysis showed mono-substituted isomer (1%), di-substituted isomer (4%), tri-substituted isomer (20%), tetra-substituted isomer (59%), penta-substituted isomer (11%). In addition 4% of methylene-bridged products and other oligomeric materials were identified in the product. Oxidation Inhibition Time measured by PDSC @ 160° C. was 72 minutes at 0.25 wt %%, 124 minutes at 0.50% wt %, and 187 minutes at 0.75 wt % loading.

Example 4

Thiophene and 2,6-di-tert-butyl-4-methoxymethylphenol (1:3 ratio)

The same procedure as example 1 was used, except a thiophene/2,6-di-tert-butyl-4-methoxymethylphenol mole ratio of 1:3 was used. A solid product, mp 53° C., was isolated. HPLC Analysis showed mono-substituted isomer (3%), di-substituted isomer (5%), tri-substituted isomer (13%), tetra-substituted isomer (34%), penta-substituted isomer (28%). In addition 13% of methylene-bridged products and other oligomeric materials were identified in the product. Oxidation Inhibition Time measured by PDSC @ 160° C. was 72 minutes at 0.25 wt %%, 124 minutes at 0.50% wt %, and 187 minutes at 0.75 wt % loading.

Example 5

Thiophene and 2,6-di-tert-butyl-4-methoxymethylphenol (1:2 ratio) in toluene

A three-necked round-bottomed flask was equipped with an addition funnel, magnetic stirrer, temperature probe, and a condenser. Thiophene (0.1 mol, 8.4 g) was dissolved in toluene (40 mL) and sulfuric acid (6 mL of 80%) was added at room temperature. A solution of 2,6-di-tert-butyl-4-methoxymethylphenol (0.2 mol, 50 g) in toluene (170 mL) was added at 50° C. over 45 minutes. The reaction mixture was heated to 110° C. and was refluxed for 3 hrs. NMR analysis showed complete conversion of the starting material. The acid phase was separated and the organic phase was washed with water (30 mL), dilute sodium hydroxide to pH 7-8, water (30 mL), and dried over magnesium sulfate. Evaporation of solvent under reduced pressure afforded a viscose oil which solidified on standing at room temperature. HPLC Analysis showed mono-substituted isomer (21%), di-substituted isomer (34%), tri-substituted isomer (25%), tetra-substituted isomer (9%), penta-substituted isomer (10%). In addition 10% of methylene-bridged products and other oligomeric materials were identified in the product. Oxidation Inhibition Time measured by PDSC @ 160° C. was 84 minutes at 0.25 wt %%, 131 minutes at 0.50% wt %, and 184 minutes at 0.75 wt % loading.

Example 6

Thiophene and 2,6-di-tert-butyl-4-methoxymethylphenol (1:3 ratio) in toluene

A three-necked round-bottomed flask was equipped with an addition funnel, magnetic stirrer, temperature probe, and a condenser. Thiophene (0.1 mol, 8.4 g) was dissolved in toluene (40 mL) and sulfuric acid (6 mL of 80%) was added at room temperature. A solution of 2,6-di-tert-butyl-4-methoxymethylphenol (0.3 mol, 75 g) in toluene (230 mL) was added at 50° C. over one hour. The reaction mixture was heated to 110° C. and was refluxed for 3 hrs. NMR analysis showed complete conversion of the starting material. The acid phase was separated and the organic phase was washed with water (30 mL), dilute sodium hydroxide to pH 7-8, water (30 mL), and dried over magnesium sulfate. Evaporation of solvent under reduced pressure afforded a viscose oil which solidified on standing at room temperature. HPLC Analysis showed mono-substituted isomer (7%), di-substituted isomer (21%), tri-substituted isomer (29%), tetra-substituted isomer (19%), penta-substituted isomer (4%). In addition 16% of methylene-bridged products and other oligomeric materials were identified in the product.

Example 7

Thiophene and 2,6-di-tert-butyl-4-methoxymethylphenol (No Solvent)

A solution of 2,6-di-tert-butyl-4-methoxymethylphenol (5 g) in thiophene (20 mL) was added to a stirred mixture of sulphuric acid (0.5 mL of 80%) and thiophene (10 mL) at room temperature. The reaction mixture was stirred at room temperature overnight. NMR analysis showed complete conversion of the starting material. The acid phase was removed and the crude reaction mixture was diluted with dichloromethane (20 mL) and it was washed with water (10 mL) and dried over magnesium sulfate. Solvent was removed under aspirator pressure followed by distillation of excess thiophene at 1-2 mmHg and 60° C. The product was an orange oil at room temperature. HPLC analysis showed mono-substituted product (91%), and di-substituted product (2%). In addition 6% of methylene-bridged products and other oligomeric materials were identified in the product.

Example 8

Thiophene and 2,6-di-tert-butyl-4-methoxymethylphenol (No Solvent with Amberlyst® Catalyst)

To a solution of 2,6-di-tert-butyl-4-methoxymethylphenol (15 g) in thiophene (50 mL) was added Amberlyst® 35 and the resulting mixture was refluxed for 23 hrs. NMR Analysis showed complete conversion of the starting material. After cooling to room temperature, the reaction mixture was filtered and the filtrate was concentrated as described in example 7. HPLC analysis of the resulting oil showed mono-substituted product (70%), di-substituted product (21%), and tri-substituted product (3%). In addition 6% of methylene-bridged products and other oligomeric materials were identified in the product. Oxidation Inhibition Time measured by PDSC @ 160° C. was 87 minutes at 0.25 wt %%, 119 minutes at 0.50% wt %, and 157 minutes at 0.75 wt % loading.

Example 9

Furan and 2,6-di-tert-butyl-4-methoxymethylphenol (1:3 ratio)

A three-necked round-bottomed flask was equipped with an addition funnel, magnetic stirrer, temperature probe, and a condenser. A solution of furan (0.1 mol, 6.8 g) in dichloromethane (20 mL) was added to a solution of 2,6-di-tert-butyl-4-methoxymethylphenol (0.3 mol, 75 g) in dichloromethane (200 mL) and sulphuric acid (3 mL of 80%) at room temperature over about 10 minutes. The reaction mixture was first stirred at room temperature overnight and refluxed for 4 hrs. NMR analysis showed complete conversion of the starting material. The acid phase was separated and the organic phase was washed with water (30 mL), dilute sodium hydroxide to pH 7-8, water (30 mL), and dried over magnesium sulfate. Evaporation of solvent under reduced pressure afforded a viscose oil which solidified on standing at room temperature. HPLC Analysis showed mono-substituted isomer (3%) and di-substituted isomer (15%). In addition about 80% of methylene-bridged products and other oligomeric materials were identified in the product. Oxidation Inhibition Time measured by PDSC @ 160° C. was 57 minutes at 0.25 wt %%, 69 minutes at 0.50% wt %, and 78 minutes at 0.75 wt % loading.

Example 10

Furan and 2,6-di-tert-butyl-4-methoxymethylphenol (No Solvent)

A three-necked round-bottomed flask was equipped with an addition funnel, magnetic stirrer, temperature probe, and a condenser. A solution of 2,6-di-tert-butyl-4-methoxymethylphenol (25 g) in furan (100 L) was added to a stirred mixture of furan (50 mL) and sulphuric acid (5 mL of 80%) in 15 minutes. The reaction mixture was stirred at room temperature for 3 hrs. Then it was filtered through a short Celite bed and the filtrate was concentrated under reduced pressure. The oily residue was dissolved in hexanes (60 mL) and the resulting solution was washed with water (30 mL), dilute sodium hydroxide to pH 7-8, water (30 mL), and dried over magnesium sulfate. Evaporation of solvent under reduced pressure afforded a viscose oil which solidified on standing at room temperature. HPLC Analysis showed mono-substituted isomer as the major product (91%). Oxidation Inhibition Time measured by PDSC @ 160° C. was 53 minutes at 0.25 wt %%, 63 minutes at 0.50% wt %, and 69 minutes at 0.75 wt % loading.

What is claimed:

1. A macromolecular reaction product comprising (a) one or more i) heterocyclic compounds substituted with one 3,5-di-hydrocarbyl-4-hydroxylbenzyl group; ii) heterocyclic compounds substituted with two 3,5-di-hydrocarbyl-4-hydroxylbenzyl groups; iii) heterocyclic compounds substituted with three 3,5-di-hydrocarbyl-4-hydroxylbenzyl groups; iv) heterocyclic compounds substituted with four 3,5-di-hydrocarbyl-4-hydroxylbenzyl groups; or v) heterocyclic compounds substituted with five 3,5-di-hydrocarbyl-4-hydroxylbenzyl groups; and (b) one or more methylene-bridged heterocyclic compounds substituted with one or more 3,5-di-hydrocarbyl-4-hydroxylbenzyl groups, wherein the methylene-bridge is between two heterocyclic groups, wherein said macromolecular reaction product is liquid at room temperatures or a solid that melts at less than about 100° C., and are capable of being dissolved in liquid hydrocarbon solvents.

2. A macromolecular reaction product comprising (a) i) less than about 10 wt. % of one or more heterocyclic compounds substituted with one 3,5-di-hydrocarbyl-4-hydroxylbenzyl group; ii) less than about 25 wt. % of one or more heterocyclic compounds substituted with two 3,5-di-hydrocarbyl-4-hydroxylbenzyl groups; iii) greater than about 15 wt. % of one or more heterocyclic compounds substituted with three 3,5-di-hydrocarbyl-4-hydroxylbenzyl groups; greater than 40 wt. % of at least one of iv) one or more heterocyclic compounds substituted with four 3,5-di-hydrocarbyl-4-hydroxylbenzyl groups, v) one or more heterocyclic compounds substituted with five 3,5-di-hydrocarbyl-4-hydroxylbenzyl groups, or combinations of iv) and v); and (b) one or more methylene-bridged heterocyclic compounds substituted with one or more 3,5-di-hydrocarbyl-4-hydroxylbenzyl groups, wherein the methylene-bridge is between two heterocyclic groups, wherein all wt. % are based on the total weight of the macromolecular reaction product, and said macromolecular reaction product is liquid at room temperature or solids that melt at less than about 100° C.

3. The macromolecular reaction product according to claim 2 wherein said macromolecular reaction product comprises (a) i) less than about 5 wt. %, of one or more heterocyclic compounds substituted with one 3,5-di-hydrocarbyl-4-hydroxylbenzyl group, ii) less than about 15 wt. %, of one or more heterocyclic compounds substituted with two 3,5-di-hydrocarbyl-4-hydroxylbenzyl groups; iii) in the range of from about 15 wt. % to about 40 wt. % of one or more heterocyclic compounds substituted with three 3,5-di-hydrocarbyl-4-hydroxylbenzyl groups; iv) in the range of from about 10 wt % to about 70 wt. % of one or more heterocyclic compounds substituted with four 3,5-di-hydrocarbyl-4-hydroxylbenzyl groups; v) in the range of from about 5 wt % to about 45 wt. % of one or more heterocyclic compounds substituted with five 3,5-di-hydrocarbyl-4-hydroxylbenzyl groups; and (b) in the range of from about 1 wt % to about 15 wt. % of one or more methylene-bridged heterocyclic compounds substituted with one or more 3,5-di-hydrocarbyl-4-hydroxylbenzyl groups, wherein all wt. % are based on the total weight of the macromolecular reaction product.

4. The macromolecular reaction product according to claim 2 wherein said macromolecular reaction product comprises one or more compounds represented by the following general formula, Formula IV:

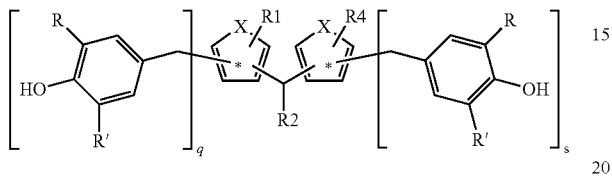

wherein each X is independently sulfur, oxygen, or nitrogen; R and R' are hydrocarbyl, and each R1 and R4 are independently hydrogen or hydrocarbyl; R2 is hydrogen, q and s are independently 1 or 2.

5. The macromolecular reaction product according to claim 2 wherein said macromolecular reaction product comprises one or more compounds represented by Formula V:

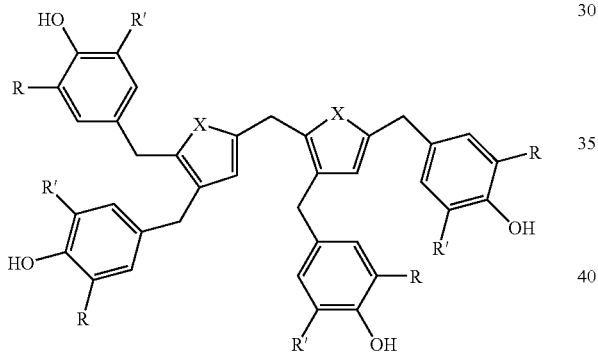

wherein each X is independently sulfur, oxygen, or nitrogen; and R and R' are hydrocarbyl.

6. The macromolecular reaction product according to claim 1 wherein said one or more methylene-bridged heterocyclic compounds substituted with one or more 3,5-di-hydrocarbyl-4-hydroxylbenzyl groups are represented by Formula IV, Formula V, or Formula IV and Formula V.

7. A composition comprising:
a) one or more organic materials that are susceptible to oxidation in the presence of air or oxygen selected from at least one oil of lubricating viscosity selected from Group I, II, and III mineral oils, poly-alpha-olefins, synthetic esters, gas to liquid derived oils, bio-based oils, internal combustion engine oils, railroad and marine lubricants, natural gas engine oils, gas turbine oils, steam turbine oils, aviation turbine oils, rust and oxidation oils, hydraulic fluids, compressor fluids, slideway oils, quench oils, manual and automatic transmission fluids, gear oils, and greases;
b) an antioxidant product containing:
i) less than about 10 wt. %, of one or more heterocyclic compounds substituted with one 3,5-di-hydrocarbyl-4-hydroxylbenzyl group;
ii) less than about 20 wt. %, of one or more heterocyclic compounds substituted with two 3,5-di-hydrocarbyl-4-hydroxylbenzyl groups;
iii) in the range of from about 15 wt. % to about 40 wt. % of one or more heterocyclic compounds substituted with three 3,5-di-hydrocarbyl-4-hydroxylbenzyl groups;
iv) in the range of from about 10 wt % to about 70 wt. % of one or more heterocyclic compounds substituted with four 3,5-di-hydrocarbyl-4-hydroxylbenzyl groups;
v) in the range of from about 5 wt % to about 45 wt. % of one or more heterocyclic compounds substituted with five 3,5-di-hydrocarbyl-4-hydroxylbenzyl groups;
vi) in the range of from about 1 wt % to about 15 wt. % of one or more methylene-bridged heterocyclic compounds substituted with one or more 3,5-di-hydrocarbyl-4-hydroxylbenzyl groups, wherein the methylene-bridge is between two heterocyclic groups,
wherein all wt. % are based on the total weight of the macromolecular reaction product; and
c) one or more dispersants, detergents, anti-wear additives, extreme pressure additives, corrosion inhibitors, rust inhibitors, friction modifiers, metal deactivators, lubricity agents, pour point depressants, antiknock agents, anti-icing agents, viscosity index modifiers, emulsifiers, demulsifiers, seal swell agents, solubilizing agents, antifoam agents, other antioxidants or stabilizers, diluents, solvents, carrier fluids, Zinc dialkyldithiophosphate, at least one conventional hindered phenolic antioxidant, at least one conventional alkylated diphenylamine antioxidant, at least one organomolybdenum compound, at least one alkylated diphenylamine and at least one organomolybdenum compound, at least one phosphorus-free anti-wear or extreme pressure additive, at least one molybdenum-containing or boron-containing dispersant, at least one organoboron compound, at least one organoboron compound and at least one conventional alkylated diphenylamine, at least one sulfurized antioxidant, EP (extreme pressure) additive or anti-wear additive, at least one conventional alkylated diphenylamine along with at least one (i) sulfurized antioxidant, (ii) EP additive, (iii) anti-wear additive, and (iv) organoboron compound.

8. A macromolecular reaction product mixture of claim 1 formed by bringing together components comprising:
(A) a sterically hindered 4-alkoxymethyl-2,6-dihydrocarbylphenol or 4-hydroxymethyl-2,6-dihydrocarbylphenol;
(B) at least one heterocyclic compound which is a monocyclic or polycyclic compound wherein:
a) the monocyclic group of the monocyclic compound is fully conjugated and has as the sole heteroatom(s) in the fully conjugated ring thereof (i) one nitrogen atom, one sulfur atom, or one oxygen atom, (ii) one sulfur and one nitrogen atom, one sulfur and one oxygen atom, or one nitrogen and one oxygen atom, or (iii) two nitrogen atoms, two sulfur atoms, or two oxygen atoms, or
b) at least one of the cyclic groups of the polycyclic compound is fully conjugated and has as the sole heteroatom(s) in the fully conjugated ring thereof (i) one nitrogen atom, one sulfur atom, or one oxygen atom, (ii) one sulfur and one nitrogen atom, one sulfur and one oxygen atom, or one nitrogen and one oxygen atom, or (iii) two nitrogen atoms, or two sulfur atoms, or two oxygen atoms;

(C) an alkylation catalyst, and
(D) optionally, an organic solvent.

9. The macromolecular reaction product mixture of claim 8, wherein said 4-alkoxymethyl-2,6-dihydrocarbylphenol or 4-hydroxymethyl-2,6-dihydrocarbylphenol is 4-hydroxymethyl-2-tert-butyl-6-methylphenol, 4-hydroxymethyl-2,6-di-tert-butylphenol, 4-methoxymethyl-2-tert-butyl-6-methylphenol or 4-methoxymethyl-2,6-di-tert-butylphenol.

10. The macromolecular reaction product mixture of claim 8, wherein said heterocyclic compound is pyrrole, imidazole, pyrazole, pyridine, pyrimidine, pyrazine, phenazine, thiophene, 2-benzothiophene, dibenzothiophene, dithiine, benzodithiine, indole, quinoline, acridine, carbazole, oxazole, isoxazole, thiazole, and isothiazole, furan, 2-benzofuran, 1,4-dioxin, benzodioxin, dibenzodioxin, or dibenzofuran.

11. The macromolecular reaction product mixture of claim 8, wherein said heterocyclic compound is thiophene or furan.

12. The macromolecular reaction product mixture of claim 8, wherein a molar ratio of (B) to (A) used in the reaction ranges from 1:1 to 1:10.

* * * * *

UNITED STATES PATENT AND TRADEMARK OFFICE
CERTIFICATE OF CORRECTION

PATENT NO.       : 8,410,084 B2
APPLICATION NO.  : 12/444181
DATED            : April 2, 2013
INVENTOR(S)      : Sabahi et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 677 days.

Signed and Sealed this
First Day of September, 2015

Michelle K. Lee
*Director of the United States Patent and Trademark Office*